US00PP18746P2

(12) United States Plant Patent
Vlielander

(10) Patent No.: US PP18,746 P2
(45) Date of Patent: Apr. 22, 2008

(54) *KALANCHOE* PLANT NAMED 'FIGRACIOSA'

(50) Latin Name: *Kalanchoe blossfeldiana*
Varietal Denomination: Figraciosa

(75) Inventor: Ike Vlielander, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 11/637,863

(22) Filed: Dec. 12, 2006

(51) Int. Cl.
*A01H 5/00* (2006.01)

(52) U.S. Cl. ..... Plt./339
(58) Field of Classification Search ..... Plt./339
See application file for complete search history.

(56) References Cited

PUBLICATIONS

GTITM UPOVROM Citation for 'Figraciosa'as per QZ PBR 20060413; Feb. 7, 2006.*

* cited by examiner

*Primary Examiner*—Kent Bell
(74) *Attorney, Agent, or Firm*—C. A. Whealy

(57) ABSTRACT

A new and distinct cultivar of *Kalanchoe* plant named Figraciosa, characterized by its upright, strong and uniform growth habit; freely branching plant habit; glossy leaves; uniform, freely and early flowering habit; pink and pale pink bi-colored flowers; and excellent postproduction longevity.

1 Drawing Sheet

Botanical designation: *Kalanchoe blossfeldiana.*
Cultivar denomination: 'FIGRACIOSA'.

BACKGROUND OF THE INVENTION

The present invention relates to a new and distinct cultivar of *Kalanchoe,* botanically known as *Kalanchoe blossfeldiana,* and hereinafter referred to by the name 'Figraciosa'.

The new *Kalanchoe* is a product of a planned breeding program conducted by the Inventor in De Lier, The Netherlands. The objective of the breeding program is to create new freely-branching and freely-flowering *Kalanchoe* cultivars with attractive foliage and flower coloration.

The new *Kalanchoe* originated from a cross-pollination made by the Inventor in De Lier, The Netherlands in November, 2000, of a proprietary *Kalanchoe blossfeldiana* selection identified as FK 3932, not patented, as the female, or seed, parent with the *Kalanchoe blossfeldiana* cultivar Lokon, not patented, as the male, or pollen, parent. The cultivar Figraciosa was discovered and selected by the Inventor as a flowering plant from within the progeny of the stated cross-pollination in a controlled environment in De Lier, The Netherlands.

Asexual reproduction of the new *Kalanchoe* by vegetative terminal cuttings in a controlled environment in De Lier, The Netherlands since the autumn of 2002, has shown that the unique features of this new *Kalanchoe* are stable and reproduced true to type in successive generations.

SUMMARY OF THE INVENTION

The cultivar Figraciosa has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Fragraciosa'. These characteristics in combination distinguish 'Figraciosa' as a new and distinct cultivar of *Kalanchoe:*

1. Upright, compact and uniform growth habit.
2. Freely branching plant habit.
3. Glossy leaves.
4. Uniform, freely and early flowering habit.
5. Pink and pale pink bi-colored flowers.
6. Excellent postproduction longevity.

Plants of the new *Kalanchoe* can be compared to plants of the female parent selection. Plants of the new *Kalanchoe* differ from plants of the female parent selection in the following characteristics:

1. Plants of the new *Kalanchoe* are more compact than plants of the female parent selection.
2. Plants of the new *Kalanchoe* are more freely branching than plants of the female parent selection.
3. Plants of the new *Kalanchoe* have smaller leaves than plants of the female parent selection.
4. Plants of the new *Kalanchoe* and the female parent selection differ in flower color.

Plants of the new *Kalanchoe* can be compared to plants of the male parent, the cultivar Lokon. Plants of the new *Kalanchoe* differ from plants of the cultivar Lokon in the following characteristics:

1. Plants of the new *Kalanchoe* are not as compact as plants of the cultivar Lokon.
2. Plants of the new *Kalanchoe* are more freely branching than plants of the cultivar Lokon.
3. Plants of the new *Kalanchoe* and the cultivar Lokon differ in flower color.

Plants of the new *Kalanchoe* can be compared to plants of the *Kalanchoe blossfeldiana* cultivar Petero, disclosed in U.S. Plant Pat. No. 12,155. In side-by-side comparisons conducted in De Lier, The Netherlands, plants of the new

*Kalanchoe* differed from plants of the cultivar Petero in the following characteristics:

1. Plants of the new *Kalanchoe* were smaller than plants of the cultivar Petero.
2. Plants of the new *Kalanchoe* had smaller leaves than plants of the cultivar Petero.
3. Plants of the new *Kalanchoe* and the cultivar Petero differed in flower color.

BRIEF DESCRIPTION OF THE PHOTOGRAPH

The accompanying colored photograph illustrates the overall appearance of the new *Kalanchoe,* showing the colors as true as it is reasonably possible to obtain in colored reproductions of this type. Colors in the photograph may differ slightly from the color values cited in the detailed botanical description which accurately describe the colors of the new *Kalanchoe*. The photograph comprises a side perspective view of a typical flowering plant of 'Figraciosa' grown in a container.

DETAILED BOTANICAL DESCRIPTION

The aforementioned photograph and following observations, measurements and values describe plants grown in De Lier, The Netherlands in a glass-covered greenhouse during the autumn and under conditions which closely approximate commercial production. During the production of the plants, day temperatures ranged from 19° C. to 26° C., night temperatures ranged from 20° C. to 21° C. and light levels ranged from 10,000 lux to 50,000 lux. Unrooted cuttings were directly stuck in 10-cm containers and received long day/short night conditions (more than 14 hours of light) for about four weeks; plants then received photoinductive short day/long night conditions (minimum 14 hours darkness) until flowering. Plants were about 14 weeks old when the photographs and the description were taken. In the detailed description, color references are made to The Royal Horticultural Society Colour Chart, 1995 Edition, except where general terms of ordinary dictionary significance are used.

Botanical classification: *Kalanchoe blossfeldiana* cultivar Figraciosa.

Parentage:

*Female, or seed, parent.*—Proprietary *Kalanchoe blossfeldiana* selection identified as code number FK 3932, not patented.

*Male or pollen parent.*—*Kalanchoe blossfeldiana* cultivar Lokon, not patented.

Propagation:

*Type.*—By vegetative terminal cuttings.

*Time to initiate roots, summer.*—About eleven days at temperatures of 21° C.

*Time to initiate roots, winter.*—About 15 days at temperatures of 21° C.

*Time to produce a rooted young plant, summer.*—About 17 days at temperatures of 21° C.

*Time to produce a rooted young plant, winter.*—About 24 days at temperatures of 21° C.

*Root description.*—Fine, fibrous; greyish white in color.

*Rooting habit.*—Freely branching; dense.

Plant description:

*Plant habit.*—Upright, compact and uniform growth habit. Very freely flowering with numerous compound cymes. Inverted triangle with rounded crown. Appropriate for 10-cm to 15-cm containers. Moderately vigorous growth habit.

*Plant height at flowering.*—About 15 cm.

*Plant diameter at flowering.*—About 16 cm.

*Branching habit.*—Freely branching, usually about five to seven lateral branches develop per plant. Pinching (removal of the terminal apex) is not required but will enhance lateral branch development.

Lateral branch description:

*Length.*—About 8 cm to 13 cm.

*Diameter.*—About 3 mm to 5 mm.

*Internode length.*—About 3 cm to 4 cm.

*Aspect.*—Erect.

*Strength.*—Moderately strong.

*Texture.*—Smooth, glabrous.

*Color.*—138B.

Foliage description:

*Arrangement.*—Opposite, simple; generally symmetrical.

*Quantity per plant.*—About 6 to 11 mature leaves and about 8 to 12 generative leaves.

*Length.*—About 9.5 cm.

*Width.*—About 7 cm.

*Shape.*—Ovate to elliptic.

*Apex.*—Obtuse.

*Base.*—Obtuse.

*Margin.*—Crenate.

*Texture, upper and lower surfaces.*—Smooth, glabrous; leathery; succulent; luster, glossy.

*Venation pattern.*—Pinnate.

*Color.*—Developing and fully developed foliage, upper surface: 147A; venation, 147A. Developing and fully developed foliage, lower surface: 147B; venation, 147B.

*Petiole.*—Length: About 1.5 cm. Diameter: About 4 mm to 8 mm. Texture, upper and lower surfaces: Smooth, glabrous. Color, upper and lower surfaces: 147A.

Flower description:

*Flower arrangement and habit.*—Flowers arranged singly in compound dichasial cymes that arise from leaf axils. Uniform and freely flowering habit with usually about 25 open flowers and about 25 flower buds per lateral branch and more than 150 open flowers and flower buds per plant. Flowering continuously for at least seven weeks. Flowers persistent. Flowers not fragrant.

*Natural flowering season.*—Plants of the new *Kalanchoe* initiate and develop flowers under short day/long night conditions or during the later autumn/winter/early spring. Flower initiation and development can also be induced under artificial short day/long night conditions (at least 14 hours of darkness).

*Time to flower.*—Early flowering habit; under short day/long night photoinductive conditions, about eight to ten weeks are required. Actual time to flower is primarily dependent upon temperature and light intensity.

*Post-production longevity.*—Excellent post-production longevity; plants maintain good foliage and flower substance for about 46 days under interior environmental conditions. Individual flowers last about 18 days on the plant.

*Flower diameter.*—About 1.7 cm.

*Flower length* (*height*).—About 1.5 cm.

*Flower bud.*—Shape: Initially oblong, becoming tubular ovoid with development. Length: About 1.2 cm. Diameter: About 2 mm. Color: 56C to 68C with development.

*Petals.*—Arrangement: Four fused at the base. Length: About 7 mm. Width: About 6 mm. Aspect: Flat to slightly upright. Shape: Ovate, rounded. Apex: Acute. Margin: Entire. Texture, upper and lower surfaces: Smooth, glabrous. Color: When opening, upper surface: Center, 56C and 10C; towards the margin, 68B. When opening, lower surface: 68C and 56C. Fully opened, upper surface: Center, 56C; towards the margin, 68B. Fully opened, lower surface: 68C and 56C.

*Sepals.*—Appearance: Four fused at the base. Length: About 6 mm. Width: About 2 mm. Aspect: Erect. Shape: Oblong. Apex: Acute. Margin: Entire. Texture, upper and lower surfaces: Smooth; glabrous. Color, upper and lower surfaces: 144B.

*Peduncles.*—Length: About 3 mm. Diameter: About 1 mm. Aspect: Erect. Strength: Strong, rigid. Texture: Smooth, glabrous. Color: 144B.

*Reproductive organs.*—Androecium: Stamen number: About eight per flower. Anther shape: Elliptic, flat. Anther length: About 0.3 mm. Anther color: Close to 150D. Amount of pollen: Scarce. Pollen color: Close to 12A. Gynoecium: Pistil number: About four per flower. Pistil length: About 1 cm. Style length: About 1 cm. Style color: 138D. Stigma shape: Flat. Stigma color: 8D. Ovary color: 138D.

*Seed.*—Length: About 0.1 mm. Diameter: About 0.05 mm. Color: Close to 166C.

Temperature tolerance: Plants of the new *Kalanchoe* have been observed to tolerate temperatures from about 16° C. to about 35° C.

Pathogen/pest resistance: Plants of the new *Kalanchoe* have not been observed to be resistant to pests and pathogens common to *Kalanchoes.*

It is claimed:

1. A new and distinct *Kalanchoe* plant named 'Figraciosa' as illustrated an described.

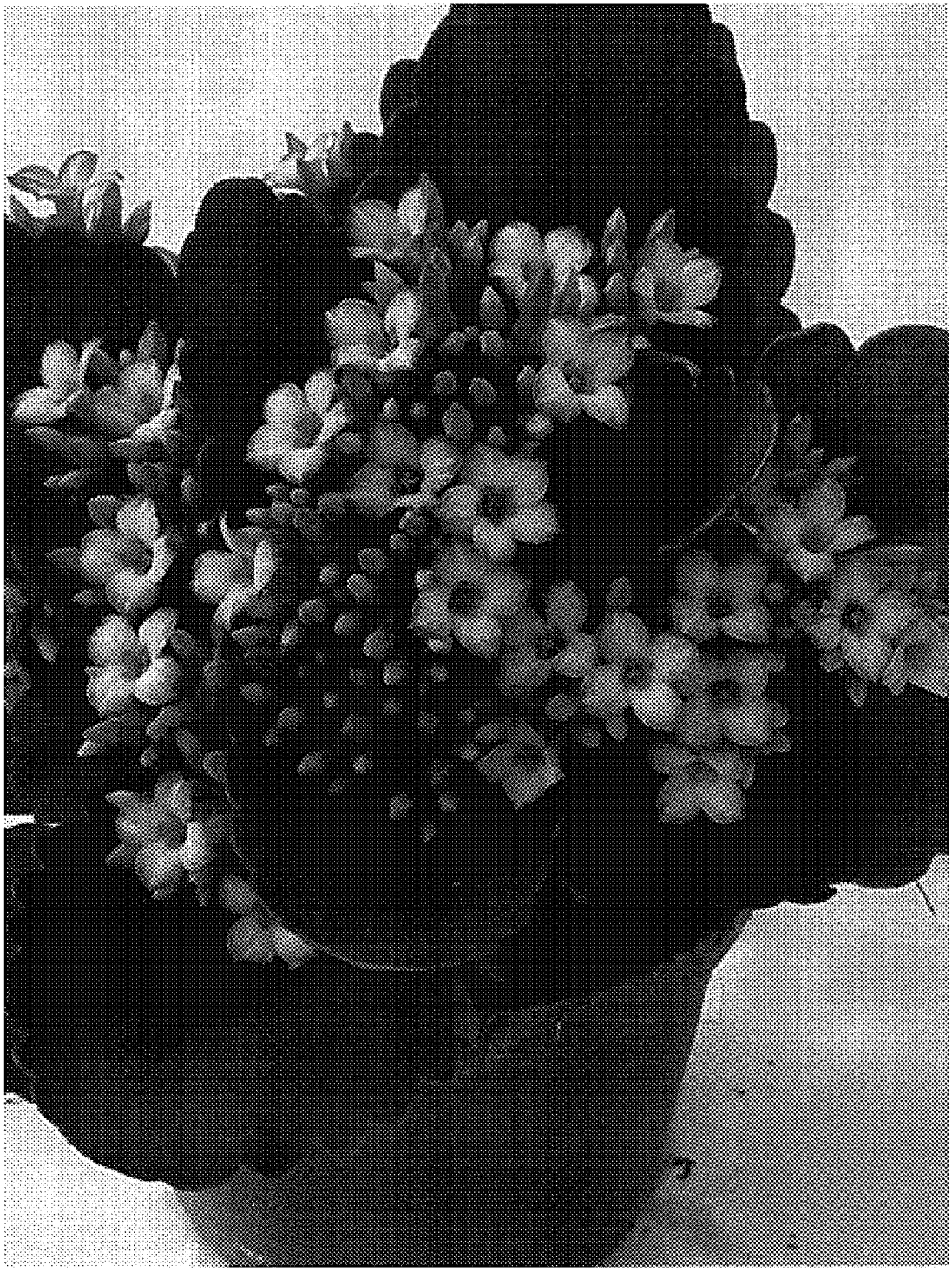

* * * * *